United States Patent [19]

Guérin

[11] 4,211,728
[45] Jul. 8, 1980

[54] METHOD OF PREPARING CARBON TETRACHLORIDE

[75] Inventor: Jean G. Guérin, Grenoble, France

[73] Assignee: Produits Chimiques Ugine Kuhlmann, Paris, France

[21] Appl. No.: 642,186

[22] Filed: Dec. 18, 1975

Related U.S. Application Data

[63] Continuation-in-part of Ser. No. 598,739, Jul. 24, 1975, abandoned.

[30] Foreign Application Priority Data

Jul. 29, 1974 [FR] France .............................. 74 26228
Jan. 8, 1975 [FR] France .............................. 75 00400

[51] Int. Cl.² ........................................... C07C 17/00
[52] U.S. Cl. ............................. 260/658 R; 260/660
[58] Field of Search ................................ 260/658 R

[56] References Cited

U.S. PATENT DOCUMENTS

| 2,160,574 | 5/1939 | Hennig | 260/658 R |
| 2,305,821 | 12/1942 | Wimmer | 260/658 R |
| 2,727,076 | 12/1955 | Warren | 260/658 R |
| 2,919,296 | 12/1959 | Thermet et al. | 260/658 R |
| 3,363,010 | 1/1968 | Schwarzenbek | 260/648 |
| 3,454,660 | 7/1969 | Chauffart et al. | 260/658 R |
| 3,928,479 | 12/1975 | Riemenschneider | 260/658 R |

Primary Examiner—Delbert E. Gantz
Assistant Examiner—Joseph A. Bosko
Attorney, Agent, or Firm—Pennie & Edmonds

[57] ABSTRACT

A method of preparing carbon tetrachloride of high purity from a crude mixture comprising lower aliphatic hydrocarbons, includes a step of liquid-phase chlorination at about 160°–200° C. and a step of vapor-phase chlorolysis at about 450°–600° C. in the presence of a metal chloride catalyst such as $MoCl_5$. This method has both economic and anti-pollution advantages in the treatment of otherwise waste residues from the industrial manufacture of, for example, vinylchloride monomer, ethylene and propylene oxides or chloroprene. Carbon tetrachloride is an old product having known utilities as solvent for resins, waxes, lacquers and for dry cleaning; also as fire-extinguisher, extractor of seeds, anthelmintic in hookworms, exterminator of grain weevils, etc.

11 Claims, 1 Drawing Figure

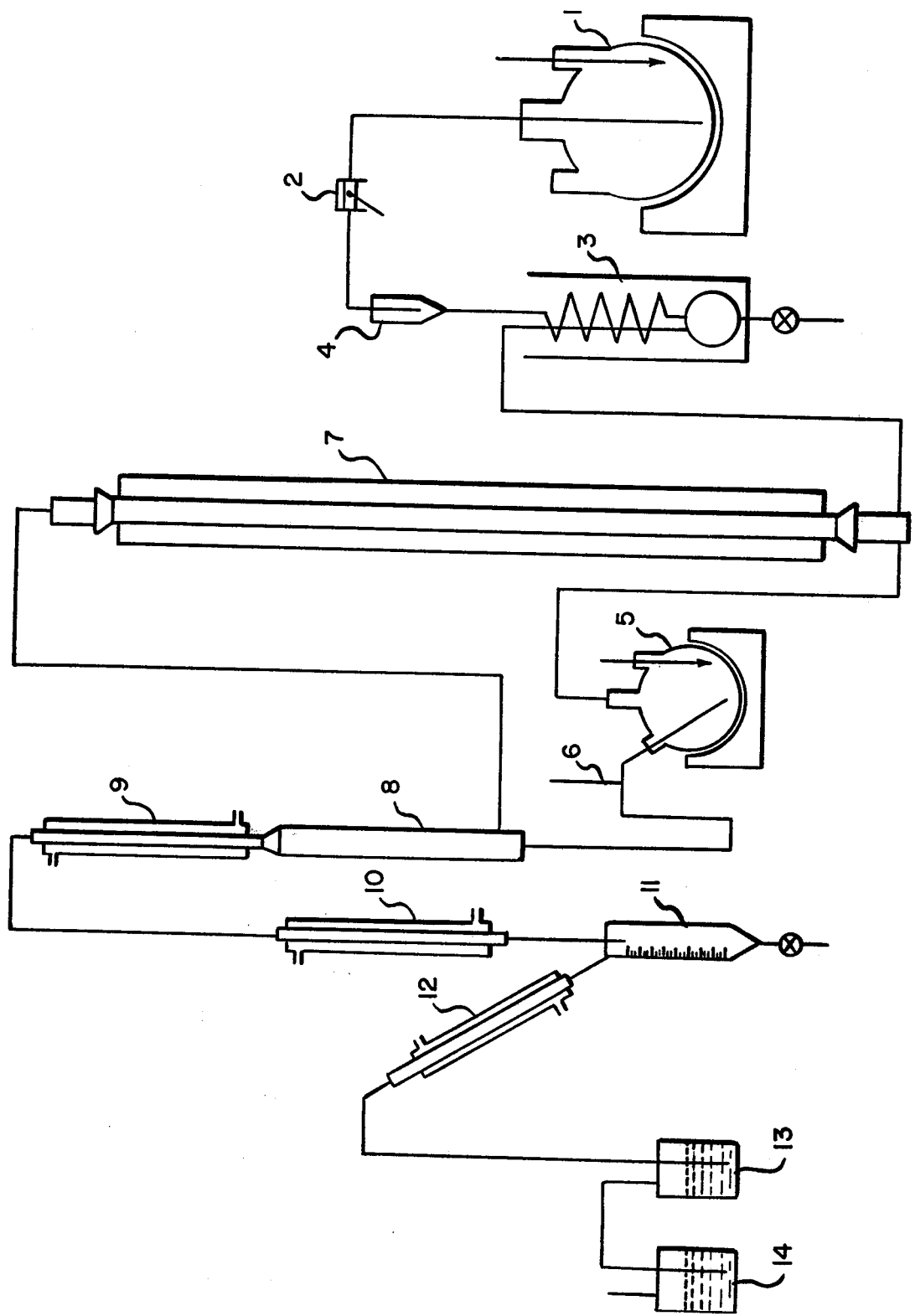

METHOD OF PREPARING CARBON TETRACHLORIDE

This application is a continuation-in-part of Serial No. 598,739, now abandoned filed July 24, 1975.

BACKGROUND OF THE INVENTION

The present invention provides a method for preparing carbon tetrachloride from lower aliphatic hydrocarbons and/or their chlorinated or oxygenated derivatives; in particular the otherwise waste residues from industrial chemical processes such as, for example, the manufacture of vinyl chloride monomer, ethylene and propylene oxides and chloroprene. Such residues primarily contain saturated or unsaturated aliphatic substances, most often chlorinated, sometimes oxygenated, typically including dichloroethane, dichloropropane, dichloroisopropylether, the chlorobutenes, the chlorobutanes, and the like; possibly including also small proportions of cyclic derivatives, in particular aromatic substances.

Simply throwing away such residues presents a serious risk of pollution. Their treatment by combustion followed by a neutralization of the hydrogen chloride liberated, increases the cost price of the main products being manufactured. Ways have therefore been sought to upgrade the residues by various means of chlorination.

U.S. Pat. No. 3,676,508 discloses a two-step process for chlorinating mixtures of aromatic and aliphatic chlorides, but this process requires a pressure of 200 to 700 atmospheres at temperatures up to 800° C. The product obtained is carbon tetrachloride. This process has the serious disadvantage of risking corrosion of the reactors, as well as the dangers of explosion and fire.

French Pat. No. 2,126,899 (see also British Pat. No. 1,316,709) proposes a process which likewise uses two steps of chlorination of essentially aliphatic chlorides. The first step takes place in the vapor phase at a temperature between 400° and 600° C., the second step takes place in liquid phase at a temperature between 100° and 200° C., in the presence of ferric chloride as catalyst. That process produces a mixture of carbon tetrachloride and perchloroethylene.

SUMMARY OF THE INVENTION

The present invention is directed to producing high yields of a particularly pure grade of carbon tetrachloride. Being free of impurities, the carbon tetrachloride produced by the method of this invention requires no further special distillation equipment for purification. In particular trichloroethylene and chloroform are absent. The method of this invention is characterized by two successive different treatments with chlorine, starting from a crude mixture containing chiefly lower aliphatic hydrocarbon derivatives as above described.

Thus, the present invention provides a method for preparing carbon tetrachloride from a crude mixture of lower aliphatic hydrocarbons or their chlorinated or oxygenated derivatives or mixtures of any of these. This method includes the steps of (i) chlorinating said crude mixture at a pressure between about 1 and 10 atmospheres and at a temperature lower than about 160°–200° C., with sufficient chlorine to form a perchlorinated product containing greater than 70% by weight chlorine, (ii) heating said perchlorinated product at a temperature higher than 250° C. in the presence of excess chlorine to form a first vapor mixture, (iii) admixing this first vapor mixture further with from 2 to 10 times its weight of the vapors of chlorinated products having the formula $C_xCl_y$ wherein x is equal to not more than 6 and y is equal to not more than 12, to form a second vapor mixture, (iv) chlorolyzing the second vapor mixture by heating it for at least two seconds at about 450°–600° C. in the presence of a metallic chloride catalyst under a pressure of about 1 to 10 atmospheres, to convert about 9 to 33% by weight of the second vapor mixture to carbon tetrachloride, (v) quenching the thus chlorolyzed vapor at about 50° C. to condense the unreacted high-boiling substances and to permit the carbon tetrachloride gaseous hydrogen chloride and excess unreacted chlorine to pass on in the gaseous state, and (vi) condensing and collecting the carbon tetrachloride.

In a preferred modification of this invention, the high-boiling substances not converted to carbon tetrachloride in the chlorolysis step and condensed in step (v) are recycled by vaporizing them and using them as all or part of the $C_xCl_y$ vapors admixed in step (iii) with the first vapor mixture from step (ii).

Also, it is preferred to carry out the chlorolysis in the presence of a large excess of chlorine and to recycle the excess unreacted chlorine from step (iv) which remains after condensation of the carbon tetrachloride in step (vi), by entering it as part or all of the chlorine used in step (i).

Likewise it is preferred to wash any excess chlorine not reacted in chlorinating step (i) with a cold chlorinated solvent and to use the thus-washed chlorine in the chlorolysis step.

This invention also includes a modification wherein the process is operated with repeated recycling of high-boiling substances not converted to carbon tetrachloride, until the vaporizer vessel gradually builds up a substantial fraction of substances having higher boiling points than tetrachloroethylene and rich in hexachlorobenzene, and recovering the hexachlorobenzene therefrom, as by distillation.

DETAILED DESCRIPTION

The first step of this method is thus to carry out a liquid-phase chlorination of the crude starting material at atmospheric pressure and at a temperature lower than 160° C., or at a pressure up to about 10 bars or about 10 atmospheres at a temperature which can reach 200° C. but no higher than 200° C. This chlorination is performed in a manner to eliminate a maximum of the hydrogen combined in the starting material. The gaseous hydrogen chloride thus formed is reusable, exemplarily in an oxychlorination unit. The perchlorinated product generally contains more than 70% by weight chlorine.

In preparation for the chlorolysis step, the perchlorinated product from the first step is vaporized at a temperature higher than 250° C. in the presence of an excess over the stoichiometric amount of chlorine and this vapor mixture is then mixed further with from about 2 to 10 times its weight of vapors of additional chlorinated products (which can preferably be the high-boiling products recycled from this chlorolysis step). The entire mixture of vapors is then submitted to the chlorolysis by heating at 450°–600° C. for a period of at least two seconds in the presence of a metallic/chloride catalyst. This operation can be carried out at atmospheric pressure or at a pressure up to about 10 bars or about 10 atmospheres. The result of this operation is that about 9 to 33% by weight of the total vapor mixture subjected to the chlorolysis is converted to carbon tetrachloride, the remaining products being recoverable for recycling.

As examples of the additional chlorinated products whose vapors are mixed with the vapors from the first-step chlorination, there can be mentioned in particular perchloroethylene, hexachloroethane, hexachlorobutadiene and hexachlorobenzene which are often produced as by-products of the main process and therefore easily available for such admixture. As indicated above, the chlorinated products recovered after the final separation of the carbon tetrachloride formed in this present method are especially suitable for the admixture, and the recycling of those products is a preferred modification of the method of this invention. In general, all the aforementioned substances suitable for admixture have the formula $C_xCl_y$ wherein x is equal to not more than 6 and y is equal to not more than 12.

Perchloroethylene which is frequently one of the essential constituents of the recycled products has proved to be particularly appropriate as the chlorinated product to be admixed. Thus, when starting up a run of this process which will at its eventual steady state include the recyling of the recovered high boiling substances, it is convenient to "prime" the vaporizing vessel with sufficient perchloroethylene as a source of the required $C_xCl_y$ vapors until this source is adequately replenished by the recycled substances.

The carbon tetrachloride formed by the chlorolysis step, then, is isolated in the vapor state while the unconverted high-boiling products and catalyst contained therewith are condensed and recycled to the chlorolysis reactor by distillation or by any other suitable procedure, in a stream of chlorine which maintains the metal or metals comprising the catalyst in the maximum valence state.

Thus, the direct end-products of this very flexible procedure are carbon tetrachloride and also 100% pure hydrochloric acid, while the high-boiling substances and excess chlorine obtained in the chlorolysis are recycled.

When the residual products to be exploited in the method of this invention contain water or slime or tarry materials, it is desirable to submit them to a preliminary distillation at atmospheric or reduced pressure to remove the offending substances and recover a clear, limpid product which is easy to chlorinate.

The chlorination which constitutes the first (liquid) step of this process is carried out by any known thermal or photochemical means or with the assistance of a peroxide catalyst or any other free-radical donor compatible with the operating conditions or by a combination of the first two of these factors, the temperature of chlorination not exceeding 160° C. when the reaction takes place at atmospheric pressure and not exceeding 200° C. when the working pressure is higher, up to about 10 bars (i.e., about 10 atmospheres). The chlorination is carried out in such a manner so as to avoid sweeping away compounds such as hexachloroethane which can sublime and can become deposited on cooling in the pipelines through which chlorine and gaseous hydrochloric acid are evacuated. Using methods which will be familiar to skilled chemical engineers, the chlorine can be confined to avoid the risk of stoppages and to minimize the plugging of the pipes.

The chlorolysis can be catalyzed by any metallic chloride or mixture of metallic chlorides, in particular chlorides of copper or silver or the metals of groups Va, VIB and VIIb of the periodic classification of elements as presented exemplarily on page 1680 of the 1961 edition of the Merriam-Webster unabridged dictionary. In particular, the metals of group Va include antimony and bismuth; the metals of group VIb include chrominum, molybdenum, tungsten and uranium; and the metals of group VIIb include manganese. Volatile metallic chlorides are especially useful, the most suitable of these being $SbCl_5$, $SbCl_3$, $MoCl_5$, $MoCl_3$, $FeCl_3$, $WCl_6$, $WCl_5$, $UCl_6$ and $UCl_4$.

The use of molybdenum pentachloride is particularly appropriate since its volatility is sufficiently low to permit an easy separation from the carbon tetrachloride produced, yet sufficiently high to permit its recycling in the vapor phase to the chlorolysis reactor. Also, the high solubility of $MoCl_5$ in the chlorinated organic substances helps to avoid its crystallization and the risk of plugging up pipes. Particularly suitable concentrations are about 5 to 50 grams molybdenum pentachloride per kilogram of high-boiling recycled product.

The metallic chlorides used to catalyze the chlorolysis can be introduced into the chlorolysis reactor as the metal chlorides themselves, generally chlorides of maximum valence, but they can equally well be introduced in the form of corresponding chlorides of lower valence or even in metallic form.

The chlorolysis reactor can be a wide tube effecting at least 2 seconds time of contact between reactants and catalyst, or a fixed bed or fluidized bed tubular reactor containing a porous inert support as, for example, activated carbon or pumice stone. In general, the use of a porous support is preferred in order to lessen the risk of plugging the equipment, as illustrated in Example 6 below.

In a particular embodiment of the method of this invention, the metallic chlorides used as catalyst, instead of being introduced into the reactor with the high-boiling chlorinated substances, can be deposited on the inert support used to fill the reaction tubes. An advantage of this mode of operation is that it permits use of metal chlorides having low volatility such as the chlorides of copper CuCl and $CuCl_2$ and the chloride of silver.

In carrying out the chlorolysis, it is always necessary to use chlorine in excess in order to obtain a good yield of carbon tetrachloride; the excess chlorine can then be used for the chlorination.

In a modification of this method, an amount of chlorine is used for the chlorolysis corresponding to 2 to 3 times the stoichiometrically equivalent amount, which results in obtainment of carbon tetrachloride with a very high degree of purity. In such case, the excess chlorine can be in amount at least sufficient to meet the total requirement of the chlorination step. When the excess of chlorine from the chlorolysis is not all used up in chlorinating, it can be separated from the hydrochloric acid obtained in chlorination by washing with a chlorinated solvent such as carbon tetrachloride or cold perchloroethylene condensed by cooling. This results in obtaining a hydrochloric acid of high purity and a grade of chlorine which is recyclable to the chlorolysis reactor.

BRIEF DESCRIPTION OF THE DRAWING

Any suitable equipment can be utilized for carrying out the chlorolysis; by way of example, a method of operating a chlorolysis is represented schematically in the drawing of FIG. 1.

The high-boiling perchlorinated substances are collected and reheated in the flask (1), from which they are pumped and sprayed at constant flow by means of volumetric proportioning pump (2) into the evaporator (3) where they are swept on by the stream of chlorine introduced at (4).

The gaseous mixture of chlorine and vaporized chlorinated products contact the vapors of the recycled mixture coming from the boiling flask or still (5), the latter being previously charged with 5 to 50 grams of volatile metallic chloride per kilogram of recycled product, as for example by using in the mixture right at the start a perchloroethylene containing a corresponding amount of the metallic chloride. Another method of introducing the catalyst consists in inserting at the foot of reactor (7), 2 to 20 grams of metallic powder or shavings and to supply chlorine before the actual start of the operation. An injection of chlorine into the still (5) is provided for at (6) in order to facilitate recycling of catalyst when this is a volatile chloride.

The combined vapors are directed through the chlorolysis tube (7) having 21 mm diameter and 2,000 mm length, filled with activated carbon, optionally impregnated with metallic chloride catalyst and heated to 500° C. The chlorolyzed mixture, chiefly consisting of perchlorinated substances having 1,2,3,4 or 6 carbon atoms per molecule of unreacted chlorine when an excess of chlorine has been used, and hydrochloric acid, is cooled by quenching at the foot of a fractionating column (8) surmounted by a condenser (9), cooled by water thermostated at 35°-70° C., having the function of a rectifier. The gaseous stream which leaves the rectifier contains the carbon tetrachloride, the hydrogen chloride and chlorine while the column (8) recycles the high-boiling condensates into the still (5). The metallic chloride is separated in column (8) and is not swept along with the vapors of carbon tetrachloride. It returns into the still (5) with the high-boiling substances in which it is soluble and from where it is reevaporated as the result of boiling and of the supplementary injection of chlorine through (6) which keeps it at its highest valence level.

At the outlet of the rectifier, carbon tetrachloride is condensed in (10) and collected in (11), then the gases are cooled to −20° C. in (12), the absorbers containing respectively water (13) and aqueous sodium hydroxide (14) retain the hydrochloric acid and the chlorine. The yields of carbon tetrachloride correspond to 80-97% of the amount calculated on the basis of the carbon content of the residues put into the process.

In the light of present industrial and social preoccupation with the struggle against pollution, as well as in the view of economic considerations, the method of the instant invention is particularly valuable as a means of using and upgrading otherwise waste materials stemming from organic chemical processes and comprising both chlorinated and non-chlorinated aliphatic hydrocarbons. As important examples of such processes there have already been mentioned the manufacture of vinyl chloride, ethylene oxide, propylene oxide and chloroprene; these are further illustrated in some of the working examples which follow. These examples serve to illustrate in a non-limiting sense the method of producing carbon tetrachloride according to this invention and show the flexibility of this method in being adaptable to treatment of a great variety of product mixtures or residues from divers sources.

EXAMPLE 1

Into a vertical reactor, crossed by an actinic radiation lamp of 40 watts power, there was charged 3,600 grams of residues from the manufacture of vinyl chloride starting with ethylene. These residues had previously been freed of solid and tarry substances by means of a "flash" distillation under reduced pressure. They comprised chiefly dichloroethane, other $C_2$, $C_3$ and even $C_4$ compounds, more or less chlorinated, and less than one percent of aromatic substances.

Over a period of the first ten hours, 500 grams/hr of chlorine were added, starting the chlorination at 60° C. and raising the temperature gradually to about 150° C. Since this chlorination was carried out in a single chlorinator, the supply of chlorine was reduced to 300 grams/hr after the tenth hour in order to limit the losses of unreacted chlorine whereas in an industrial installation having several chlorination stages, such losses would have been limited to a few percent.

A small part of the chlorine is fixed by addition but the major part reacts by substitution of hydrogen, forming hydrogen chloride which was taken up in an absorber. In this manner, nearly 80% of the hydrogen initially contained in chemical combination was eliminated.

After absorption of 3,570 grams of hydrochloric acid formed in the course of this chlorination, 7,120 grams of "perchlorinated" product were collected, shown by analysis to contain 85.7% of chlorine, which had been transferred to the flask or vessel (1) in the attached drawing. This vessel is maintained at 120° C. in order to avoid any partial crystallization of the perchlorinated solids such as $C_2Cl_6$. By means of a volumetric proportionating pump (2), there are injected 35 ml/hr of the "perchlorinated" material into the evaporator (3) operating at 280° C. while the vaporized product is entrained and mixed with a stream of chlorine at 80 grams/hr, entering at (4). This gaseous mixture meets at the foot of the chlorolysis reactor (7) the gaseous recycled mixture from the still (5). At the start the still is charged with 15 grams of $MoCl_5$ and 150 grams of perchloroethylene $C_2Cl_4$ the principal component of the recycled mixture. For the purpose of maintaining the catalyst in its maximum valence state, 20 grams/hr of chlorine are introduced at (6), allowing its partial evaporation with the vapors of the recycled mixture coming from still (5) to rise during the normal course of operation, to at least 200° C.

After passage through tube (7) which is first filled with granules of activated carbon of 5 mm. size, the chlorolyzed vapors in presence of excess chlorine are quenched at the foot of the column (8) whose condenser (9) operated at 50° C., condenses the high-boiling components but permits carbon tetrachloride to pass, carried along in the gaseous state by the excess chlorine and by the hydrogen chloride formed during the course of chlorolysis. The $CCl_4$ is condensed by means of condensers (10) and (12) and it is collected in the graduated receiver (11) which permits observing the rate of delivery. The HCl is absorbed in (13) by washing with water and the excess chlorine is absorbed in (14) by means of washing with caustic soda solution.

The operation was continued in the same manner for several-hundred hours during the course of which 60 to 65 grams/hr of CCl$_4$ were collected, while the still (5) gradually became filled with residues of higher boiling point than C$_2$Cl$_4$ and almost exclusively consisting of hexachlorobenzene, C$_6$Cl$_6$ which was purified by removal of C$_2$Cl$_4$, C$_2$Cl$_6$, C$_4$Cl$_6$ and of MoCl$_5$ by a preliminary distillation. On the average 2 to 4 grams/hr of C$_6$Cl$_6$ were produced. The 40 to 50 grams/hr of excess chlorine which were absorbed at (14) could be reused industrially at the stage of producing the "perchlorinated" substances.

EXAMPLE 2

Operating as in Example 1, 2,800 grams of residues from the production of propylene oxide were charged to the chlorination reactor. These residues consisted chiefly of dichloropropane and contained in addition some dichloroisopropyl ether. 11,000 grams of chlorine were used, the temperature rising from 50° C. at the start to 140° C. at the end. There were collected 4,635 grams of hydrochloric acid and 6,780 grams of "perchlorinated" material, shown by analysis to contain 84.2% chlorine.

This "perchlorinated" material was treated in the chlorolysis installation as in Example 1, at a rate of 35 ml/hr and 70 to 75 grams/hr of CCl$_4$ were collected, while 0.5–1.5 grams per hour of C$_6$Cl$_6$ were also formed.

EXAMPLE 3

Using the chlorination reactor described in Example 1, a mixture was charged composed of 900 grams of the residue from production of vinyl chloride and 1,800 grams of residues from the production of propylene oxide. After chlorination under the conditions of Example 1, there were obtained 6,150 grams of a "perchlorinated" mixture, liquid at ambient temperature, shown by analysis to contain 85.1% chlorine.

Treated by chlorolysis as in Example 1, this "perchlorinated" mixture produced 65 to 70 grams/hr of carbon tetrachloride and 1.5 grams/hr of hexachlorobenzene.

EXAMPLE 4

The chlorination treatment described in Example 1 was applied to 3,305 grams of residues from the production of propylene oxide specially enriched to contain 82% dichloroisopropyl ether. The "perchlorinated" product totalled 7,680 grams and was shown by analysis to contain 78.2% chlorine and 5,180 grams HCl.

The perchlorinated material was liquid at ambient temperature and was submitted to chlorolysis as in Example 1, leading to 70 to 75 grams/hr of CCl$_4$ and 1.4 to 1.6 grams/hr of C$_6$Cl$_6$. The effluent gases contained in addition to HCl, some chlorine and carbon monoxide which were converted to phosgene in the presence of light and an excess of chlorine.

EXAMPLE 5

The chlorination procedure of Example 1 was applied to 2,410 grams of residues from the production of chloroprene by chlorination of butadiene, previously freed of slimy and tarry impurities by distillation at atmospheric pressure, followed by a terminal distillation under reduced pressure. During the first hours of chlorination a substantial amount of chlorine was fixed by addition, then hydrochloric acid was evolved in proportion to the continued chlorination. In this manner, 6,730 grams of a perchlorinated product were prepared, found by analysis to contain 82.8% chlorine; and 2,550 grams of HCl.

The chlorolysis procedure of Example 1 was then applied to this perchlorinated material and led to 120 to 130 grams/hr of CCl$_4$ and 9 to 10 grams/hr of C$_6$Cl$_6$. It is to be noted that in spite of the abundance of C$_4$ substances in the chlorinated intermediate product practically no hexachlorobutadiene was formed in the high-boiling recycled product.

EXAMPLE 6

In carrying out the chlorolysis of a perchlorinated product obtained according to the method of Example 1, under the same conditions as in Example 1 except that the reactor tube (7) did not contain activated carbon, only 20 grams/hr of CCl$_4$ were produced while the fractionating column (8) and the pipes furnishing the C$_2$Cl$_6$ became plugged up causing great difficulty in operating the equipment. Although the method of this invention can be thus carried out in the absence of an activated carbon substrate, the results of this example point out the preference of having a porous support.

EXAMPLE 7

In carrying out the chlorolysis of a perchlorinated product obtained as in Example 2, under the same conditions as in Example 1 except that tube (7) was filled with pumice stone which had previously been crushed, screened, washed, dried and heated at 500° C., 27 ml/hr of perchlorinated substances was delivered from the chlorination of residues from production of propylene oxide, and after chlorolysis there were collected 60 to 65 grams/hr of CCl$_4$ along with 0.5 to 1.5 grams per hr. of C$_6$Cl$_6$.

EXAMPLE 8

Into the reactor of Example 1, there were charged 900 grams of residues from the production of propylene oxide and 300 grams/hr of chlorine and 47 liters/hr (corresponding to 92 grams/hr) of propane were sprayed into the reactor at several different levels while cooling the chlorination to 25°–30° C. After eight hours of injecting propane, the supply of propane was stopped while the flow of chlorine was increased to 500 grams/hr and the temperature was permitted to rise gradually from 30° C. to 140° C.

The total charge of chlorine was 13,500 and there was collected 6,800 grams of perchlorinated product analyzing 84.7% chlorine; and 6,440 grams of hydrochloric acid.

By treatment in the chlorolysis equipment as in Example 1, 40 ml/hr of perchlorinated product were converted to 80–85 grams/hr of CCl$_4$ along with 0.5–1.5 grams/hr of hexachlorobenzene.

EXAMPLE 9

The perchlorinated products obtained as in Example 1 are chlorolyzed as described in Example 1 except that the 150 grams of perchloroethylene charged to the still (5) are replaced by a mixture of 50 grams perchloroethylene, 50 grams hexachloroethane and 50 grams hexachlorobenene. The results obtained are not changed appreciably and, in particular, it is established that the same quantity of carbon tetrachloride is formed.

EXAMPLE 10

The chlorolysis tube is charged with activated carbon previously impregnated with CuCl in hydrochloric acid solution, dried under vacuum at 250° C. The quantity of CuCl fixed is 120 grams per 1,000 grams of activated carbon. The perchlorinated material obtained according to the procedure of Example 5 and chlorolyzed according to the conditions of Example 5 over this catalytic material produced 110 grams/hr of $CCl_4$, 7 to 8 grams per hour of $C_6Cl_6$ and 0.12 grams/hr of hexachlorobutadiene.

What is claimed:

1. A method for preparing carbon tetrachloride of high purity from a crude mixture of lower aliphatic hydrocarbons or their chlorinated or oxygenated derivatives or mixtures of any of these which method includes the steps of
   (i) chlorinating said crude mixture at a pressure between about 1 and 10 atmospheres and at a temperature lower than about 160°–200° C. with sufficient chlorine to form a perchlorinated product containing greater than 70% by weight chlorine,
   (ii) heating said perchlorinated product at a temperature higher than 250° C. in the presence of excess chlorine to form a first vapor mixture,
   (iii) admixing this first vapor mixture further with from 2 to 10 times its weight of the vapors of chlorinated products having the formula $C_xCl_y$ wherein x is equal to not more than 6 and y is equal to not more than 12, to form a second vapor mixture,
   (iv) chlorolyzing the second vapor mixture by heating it for at least two seconds at about 450°–600° C. in the presence of molybdenum pentachloride catalyst under a pressure of about 1 to 10 atmospheres, to convert about 9–33% by weight of the second vapor mixture to carbon tetrachloride,
   (v) quenching the thus chlorolyzed vapor at about 50° C. to condense the unreacted high-boiling substances and to permit the carbon tetrachloride, gaseous hydrogen chloride and excess unreacted chlorine to pass on in the gaseous state, and
   (vi) condensing and collecting the carbon tetrachloride.

2. Method of claim 1 wherein the molybdenum pentachloride is used in an amount about 5 to 50 grams per kilogram of the perchlorinated product used in step (ii).

3. Method of claim 1 wherein the chlorolyzing takes place in a reactor filled with a fixed porous support.

4. Method of claim 1 wherein the chlorolyzing takes place in a reactor comprising a fluidized-bed porous support.

5. Method of claim 3 wherein the molybdenum pentachloride catalyst is preliminarily deposited on the porous support.

6. Method of claim 1 wherein said crude mixture is a by-product of chemical manufacture of vinylchloride, ethylene oxide, propylene oxide or chloroprene.

7. Method of claim 6 wherein prior to the chlorinating step (i), any moisture, tars or slimes present in the crude mixture is first eliminated by distilling under atmospheric or reduced pressure and drying.

8. Method of claim 1 wherein the unconverted high-boiling substances condensed in step (v) are recycled by being heated to form vapors which are then used as all or part of the $C_xCl_y$ vapors admixed in step (iii) with the first vapor mixture from step (ii).

9. Method of claim 1 wherein the chlorolyzing of steps (ii), (iii) and (iv) is carried out in the presence of a large excess of chlorine, which is totally or partially reused in the chlorinating step (i).

10. Method of claim 9 wherein the chlorine is still in excess after the chlorination step (i) and wherein this latter excess is separated from hydrochloric acid by washing with a cold chlorinated solvent.

11. Method of claim 8 wherein the recycling of high-boiling substances is continued until they contain a substantial fraction of hexachlorobenzene and wherein this hexachlorobenzene is recovered by distillation.

* * * * *